US005788642A

United States Patent [19]
Hamatake et al.

[11] Patent Number: 5,788,642
[45] Date of Patent: Aug. 4, 1998

[54] IN VIVO REZERO APPARATUS FOR A PRESSURE TRANSDUCER

[75] Inventors: Bret Hamatake, Salt Lake City; Robert L. Kuster, Park City; Stephen L. Richards, South Jordan, all of Utah

[73] Assignee: Becton, Dickinson and Company, Franklin Lakes, N.J.

[21] Appl. No.: 492,175

[22] Filed: Jun. 19, 1995

[51] Int. Cl.$^6$ ........................................... A61B 5/02
[52] U.S. Cl. .................... 600/488; 73/4 R; 600/486; 600/561
[58] Field of Search ........................ 128/673, 674, 128/675, 748, 664–67, 774, 753, 756; 73/4 R

[56] References Cited

U.S. PATENT DOCUMENTS

| | | | |
|---|---|---|---|
| 4,901,735 | 2/1990 | von Berg | 128/748 |
| 5,050,297 | 9/1991 | Metzger | 29/855 |
| 5,133,358 | 7/1992 | Gustafson et al. | 128/675 |
| 5,203,340 | 4/1993 | Gustafson et al. | 128/675 X |
| 5,437,284 | 8/1995 | Trimble | 128/673 |

FOREIGN PATENT DOCUMENTS 0 492 837 A1  7/1992  European Pat. Off. .

90/11717  10/1990  WIPO .

OTHER PUBLICATIONS

OPX Innerspace device brochure by InnerSpace Medical, 1923 S.E. Main Stree, Irvine, CA.

Codman ICP Monitoring System brochure by Johnson & Johnson, Raynham, MA.

Princeton/LADD ICP Monitor brochure by Princeton Medical Corp., 225 Lowell Road, Hudson, NH.

ICP Monitoring System brochure by Steritek, 106 McLean Blvd., Paterson, NJ.

A Complete ICP System For Parenchymal, Subdural or Ventricular Monitoring brochure by Camino Laboratories, 5955 Pacific Center Blvd., San Diego, CA.

Primary Examiner—Lee S. Cohen
Assistant Examiner—Ryan Carter
Attorney, Agent, or Firm—Eric M. Lee

[57] ABSTRACT

An in vivo rezero apparatus for a pressure transducer is disclosed. This invention includes embodiments where both sides of the pressure transducer are exposed to atmospheric pressure to rezero the pressure transducer and embodiments where both sides of the pressure transducer are exposed to physiologic pressure to rezero the pressure transducer.

37 Claims, 7 Drawing Sheets

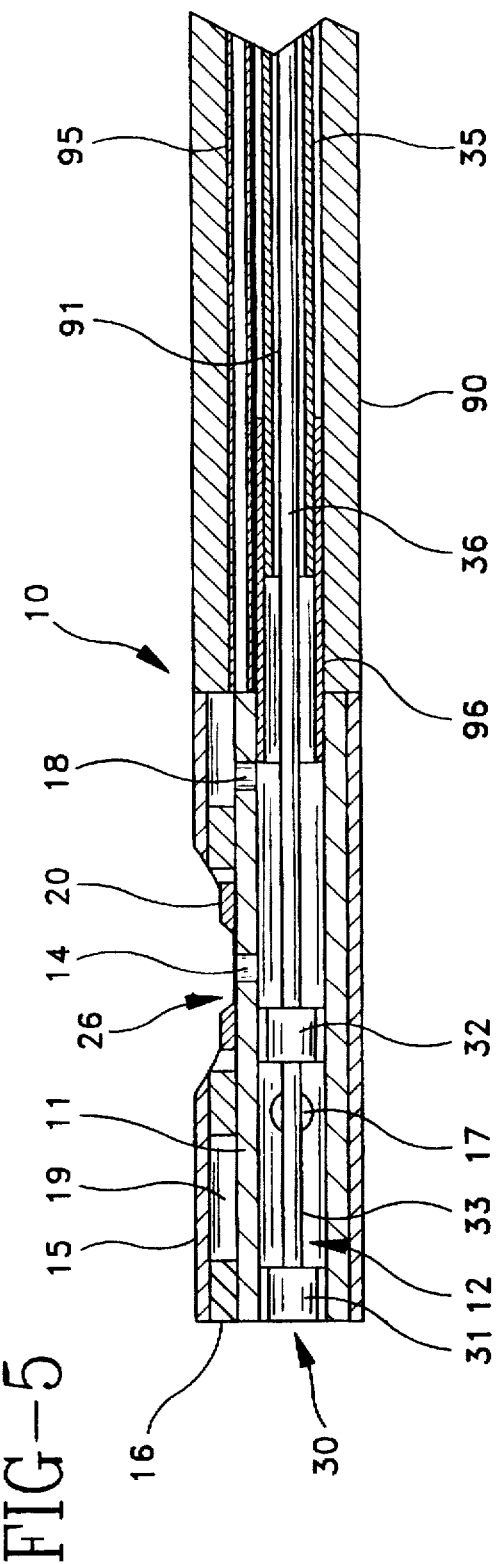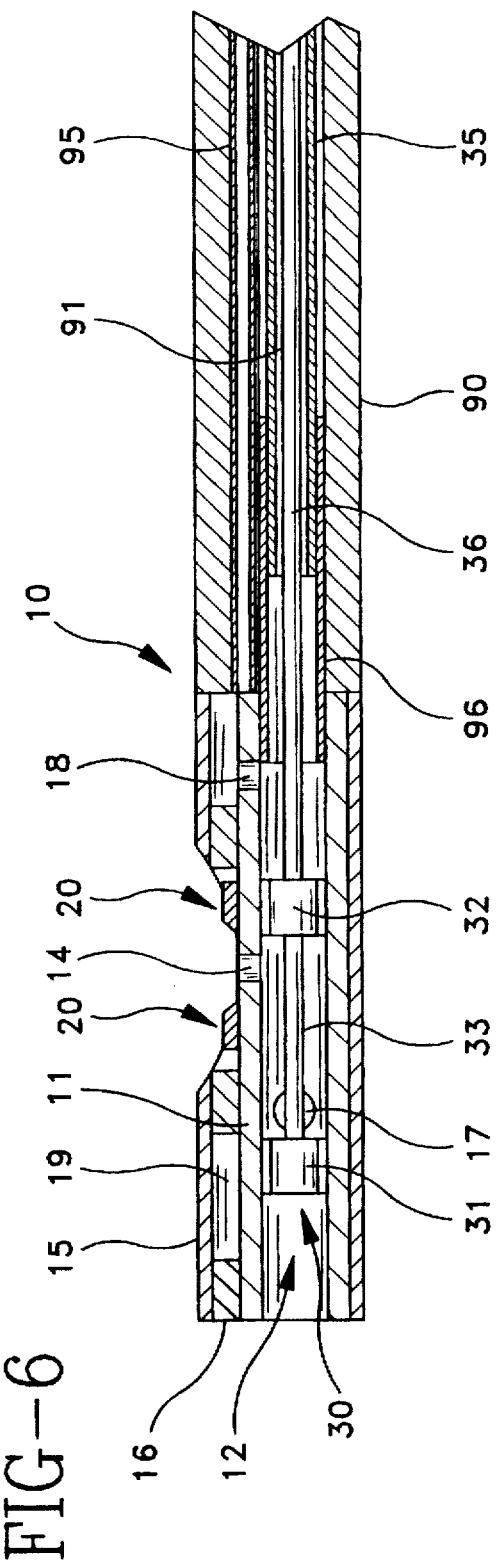

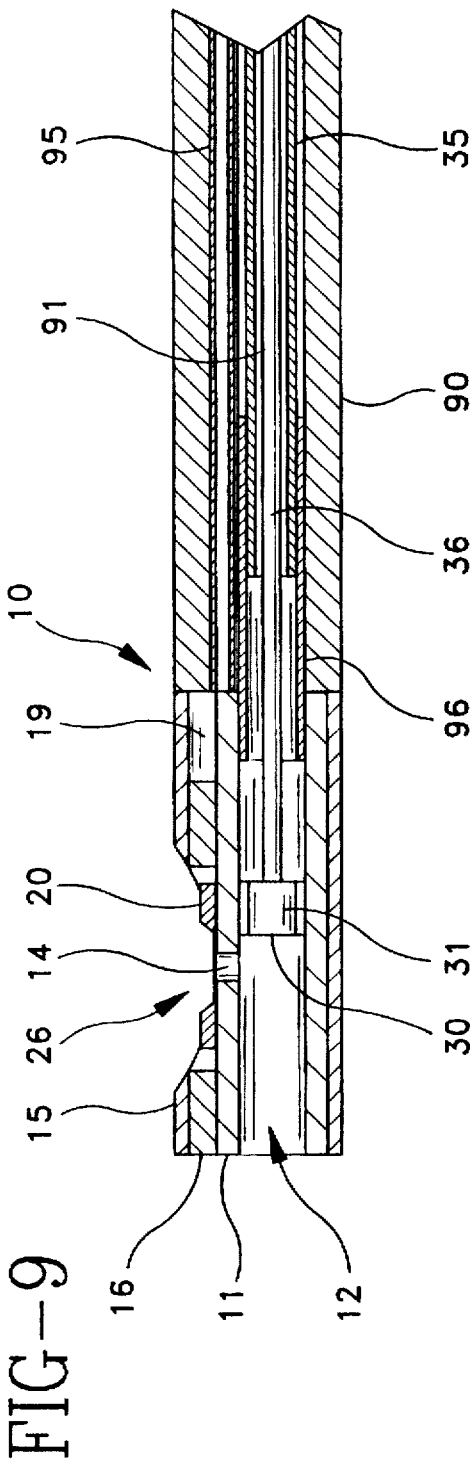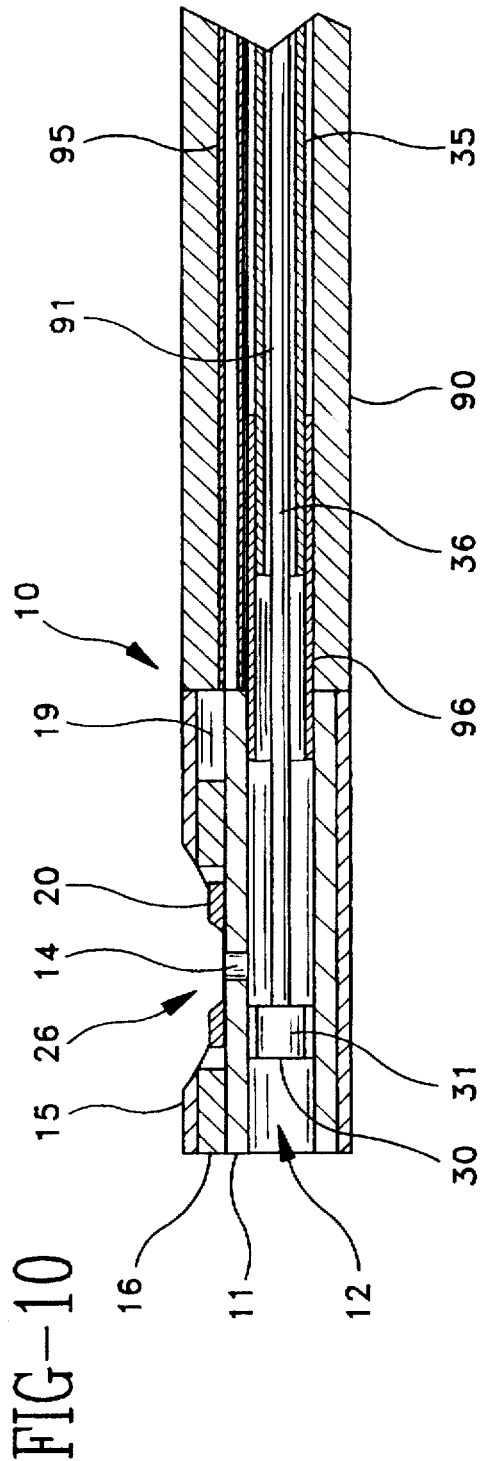

IN VIVO REZERO APPARATUS FOR A PRESSURE TRANSDUCER

BACKGROUND OF THE INVENTION

This invention relates to an apparatus that can rezero a pressure transducer in vivo.

Pressure transducers are used to monitor various patient pressures in multiple sites within the body. For example, pressure monitoring is used for hemodynamic monitoring to assess the cardio-pulmonary status of a critically ill patient. Another application where pressure monitoring is important is in patients who have experienced severe head trauma. In these head injured patients intracranial pressure (ICP) can rise due to tissue swelling or internal bleeding. Early diagnosis and treatment of brain swelling are critical to prevent secondary brain injury due to tissue ischemia.

Currently, the continuous measurement of physiologic pressures is performed using external pressure transducers. These ex vivo transducers are mounted near the patient and are connected to various physiologic locations via fluid filled tubing and catheters. Because of the inherent elasticity of the fluid filled tubing, the possibility of fluid leaks, leveling issues, and air bubbles entering the system, the external transducer system is a source of significant pressure and waveform inaccuracy. Infection is also a risk with fluid-coupled systems.

Pressure monitoring systems using an in vivo pressure transducer have solved some of these problems. However, in vivo pressure transducers suffer a unique problem not shared by external transducers. Pressure transducers that function with existing hospital monitors, both in vivo and ex vivo, supply a known or common output for a given change in pressure. Due to individual differences between transducers, each device must be zero referenced after connection to the hospital monitor. This is accomplished by exposing the pressure transducer to atmospheric pressure and then zeroing the monitor. The monitor retains this transducer response as zero pressure. Additionally, as a patient is transported throughout the hospital for diagnosis and/or treatment the pressure transducer is routinely disconnected from one monitor and connected to another at a remote location. Each time a pressure transducer is connected to a different monitor a new zero baseline must be established on that monitor. External transducers are located ex vivo and can be easily rezeroed by venting both sides of the transducer to atmospheric pressure. An in vivo pressure transducer, however, cannot be removed from the patient to vent both sides of the transducer to atmospheric pressure and to re-establish this zero baseline. Attempting to do so would expose the patient to an unacceptable risk of infection.

Thus there is a need for a device that will repeatably rezero an in vivo pressure transducer in vivo.

SUMMARY OF THE INVENTION

It is therefore an object of this invention to provide a device that will allow an in vivo pressure transducer to be rezeroed in vivo.

The in vivo rezero apparatus of this invention is comprised of a tip assembly that houses the pressure transducer and a portion of the rezero apparatus, a proximal actuator assembly that allows switching between measure and rezero modes, and a tube that connects the tip assembly to the proximal actuator assembly. In use, the tip assembly of the device is placed in the medium to be measured while the proximal actuator assembly resides ex vivo for connection to pressure monitoring equipment.

The tip assembly includes two lumens therein. It can have a bilumen configuration. Preferably the tip assembly is formed from a tube within a sleeve to create the two lumen configuration. The tube is assembled eccentrically within the sleeve such that a portion of the tube abuts a portion of the sleeve. This arrangement ensures that the tip assembly has two distinct lumens. The distal end of the tube is open while the distal end of the sleeve surrounding the tube is closed. A pressure transducer is fixed to the tube in the lumen created between the tube and sleeve. A movable seal assembly is located within the lumen of the tube.

In one embodiment of the tip assembly the tube has a first opening and a second opening through its wall so the two lumens are in fluid communication with one another. The pressure transducer is located over the first opening which is preferably closer to the distal end of the tip assembly than the second opening. A third opening is located through the walls of both the tube and the sleeve at a location where these walls are in abutting relationship. This third opening places the interior of the tube in communication with the exterior of the tip assembly. The third opening is distal to the first opening in the tube. In this embodiment only one side of the pressure transducer is ever exposed to physiological pressure.

In the pressure measurement mode, the movable seal assembly is positioned to allow physiologic pressure communication between the first opening in the tube and the third opening to the exterior of the tip assembly. Atmospheric pressure is routed from the proximal end of the device through the tube to the backside of the pressure transducer via the second opening. Physiologic pressure is transmitted through the third opening to the first opening under the pressure transducer. In this way the pressure transducer can measure physiologic pressure by using atmospheric pressure as a reference. By using an atmospheric pressure reference, the transducer is not affected by changes in barometric pressure.

When the seal assembly is positioned in the rezero mode it allows communication between the first opening under the pressure transducer through the tube to an atmospheric vent through the proximal end of the device. Atmospheric pressure is also routed from the proximal end of the device to the backside of the pressure transducer via the second opening. Thus, both sides of the pressure transducer are exposed to atmospheric pressure.

In the second embodiment of the tip assembly, the wall of the sleeve has a sidehole adjacent to the pressure transducer exposing one side of the pressure transducer to physiologic pressure. When the seal assembly is positioned in the measure mode it allows communication between the other side of the pressure transducer through the tube to an atmospheric vent through the proximal end of the device. In this situation, the pressure transducer is able to measure physiologic pressure. When the seal assembly is positioned in the rezero mode it allows communication between the exterior of the tip assembly through the third opening and to the other side of the pressure transducer through the first opening via the tube. In this position, both sides of the pressure transducer are exposed to physiologic pressure. Since the pressure transducer is a differential pressure device, this condition is equivalent to exposing both sides of the pressure transducer to atmospheric pressure. In this embodiment, there is no need for the second opening formed in the wall of the tube.

In the third embodiment of the tip assembly, there is no third opening nor any sidehole adjacent to the pressure transducer. In the measure mode, one side of the pressure transducer is exposed to physiologic pressure via the first opening and the open distal end of the tube. The other side of the pressure transducer is vented to atmospheric pressure through the second opening and through the proximal end of the device via the tube. In the rezero mode, both sides of the pressure transducer are vented to atmospheric pressure through the proximal end of the device.

In the fourth embodiment of the tip assembly, there is no second opening nor any third opening in the tube wall. However, the wall of the sleeve has a sidehole adjacent to the pressure transducer to expose one side of the pressure transducer to physiologic pressure. In the measure mode, the one side of the pressure transducer is exposed to physiologic pressure via the sidehole in the sleeve and the other side is vented to atmospheric pressure through the first opening to the proximal end of the device via the tube. In the rezero mode, the one side of the pressure transducer is still exposed to physiologic pressure via the sidehole in the sleeve while the other side is also exposed to physiologic pressure via the first opening and the open distal end of the tube. This condition is equivalent to exposing both sides of the pressure transducer to atmospheric pressure.

The proximal actuator assembly used in connection with each of the four embodiments includes a mechanism for controlling the movement of the seal assembly. The seal assembly is connected to an actuator rod that extends through the tube. The actuator rod is biased in the proximal direction by a spring located in the housing for the proximal actuator assembly. A cam device connected to a rotating knob in the proximal actuator assembly is used to move the actuator rod against the bias of the spring in the distal direction. In this way, the seal assembly can be moved between its measure mode position and its rezero mode position.

BRIEF DESCRIPTION OF THE DRAWINGS

The above and other objects and advantages of the invention will be apparent upon consideration of the following drawings and detailed description. The preferred embodiments of the present invention are illustrated in the appended drawings in which like reference numbers refer to like elements and in which:

FIG. 5 is a side elevation view in cross-section of a second embodiment of the tip assembly with the rezero apparatus in the measure mode;

FIG. 6 is a view similar to the view shown in FIG. 5 but with the rezero apparatus in the rezero mode;

FIG. 9 is a side elevation view in cross-section of a fourth embodiment of the tip assembly with the rezero apparatus in the rezero mode;

FIG. 10 is a view similar to the view shown in FIG. 9 but with the rezero apparatus in the measure mode.

DETAILED DESCRIPTION OF THE INVENTION

The in vivo rezero apparatus for a pressure transducer of this invention includes a tip assembly 10, a proximal actuator assembly 50 and a tube 90 that connects tip assembly 10 with proximal actuator assembly 50.

The pressure transducer 20 used in this device is a solid-state, silicon device employing a Wheat stone Bridge circuit configuration. It is a differential pressure device. The difference between the pressure seen at one side of pressure transducer 20 and that seen at the other side is used to determine the pressure in the environment being monitored. Atmospheric pressure is typically used as the reference for physiologic pressure measurements. Thus, one side of pressure transducer 20 must be exposed to physiologic pressure while the other side is vented to atmospheric pressure. In order to rezero pressure transducer 20, both sides of pressure transducer 20 must be exposed to atmospheric pressure or, because it is a differential pressure device, to the same pressure.

Figure 4:
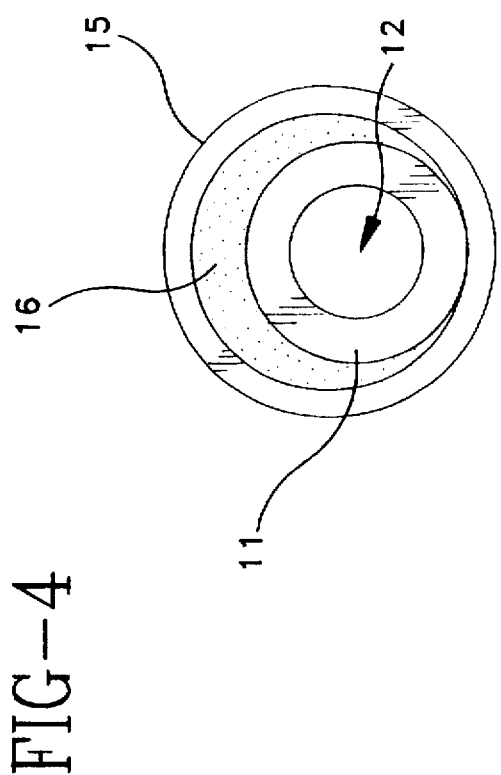
FIG. 4 is an end view of the tip assembly.

Tip assembly 10, which houses pressure transducer 20, has two lumens therein. It can have a bilumen configuration. Preferably tip assembly 10 is formed from a tube 11 within a sleeve 15. Tube 11 and sleeve 15 are non-concentric and preferably tube 11 abuts sleeve 15 as shown in FIG. 4. Tube 11 defines a lumen 12, which preferably has a circular cross-section. Tube 11 is preferably formed from ceramic, metal or polymer and is chosen for its structural as well as its non-magnetic properties. Sleeve 15 is a polymer extrusion or non-magnetic alloy and is adhered to tube 11 with an adhesive. Preferably silicone adhesive is used. The adhesive is applied between tube 11 and sleeve 15 to form a distal wall 16 that occludes the distal end of the lumen 19 formed between tube 11 and sleeve 15.

An opening 14 is located in tube 11 placing lumen 19 and lumen 12 in communication. Pressure transducer 20 is located over opening 14 and is fixed to tube 11 with an adhesive. Preferably silicone adhesive is used. Another opening 17, distal to first opening 14, extends through tube 11 and sleeve 15 at a location where tube 11 and sleeve 15 are in abutting relationship so that lumen 12 is in communication with the exterior of sleeve 15. Physiologic pressure is communicated through opening 17 into lumen 12 and through opening 14 to one side of transducer 20.

Figure 1:
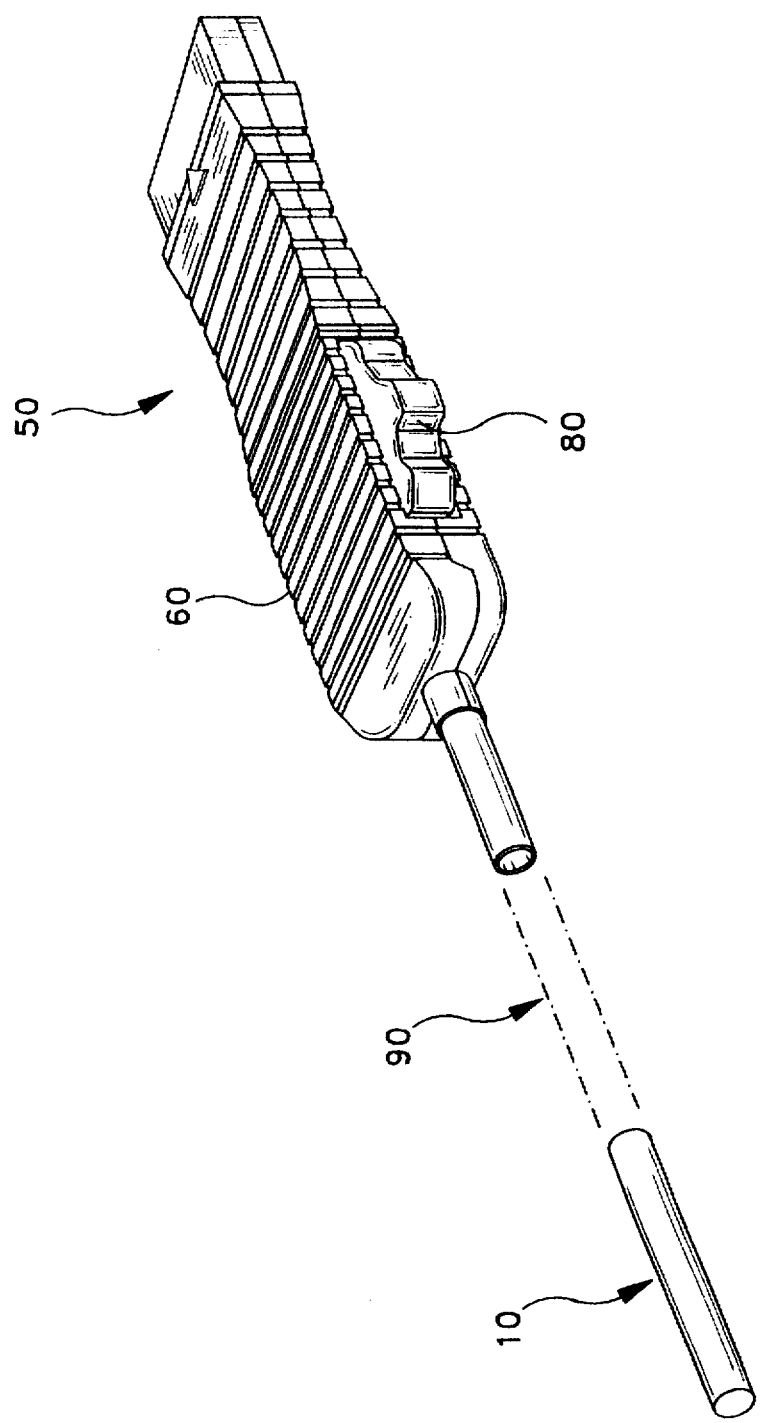
FIG. 1. is a perspective view of the in vivo rezero apparatus for a pressure transducer of this invention.
Figure 2:
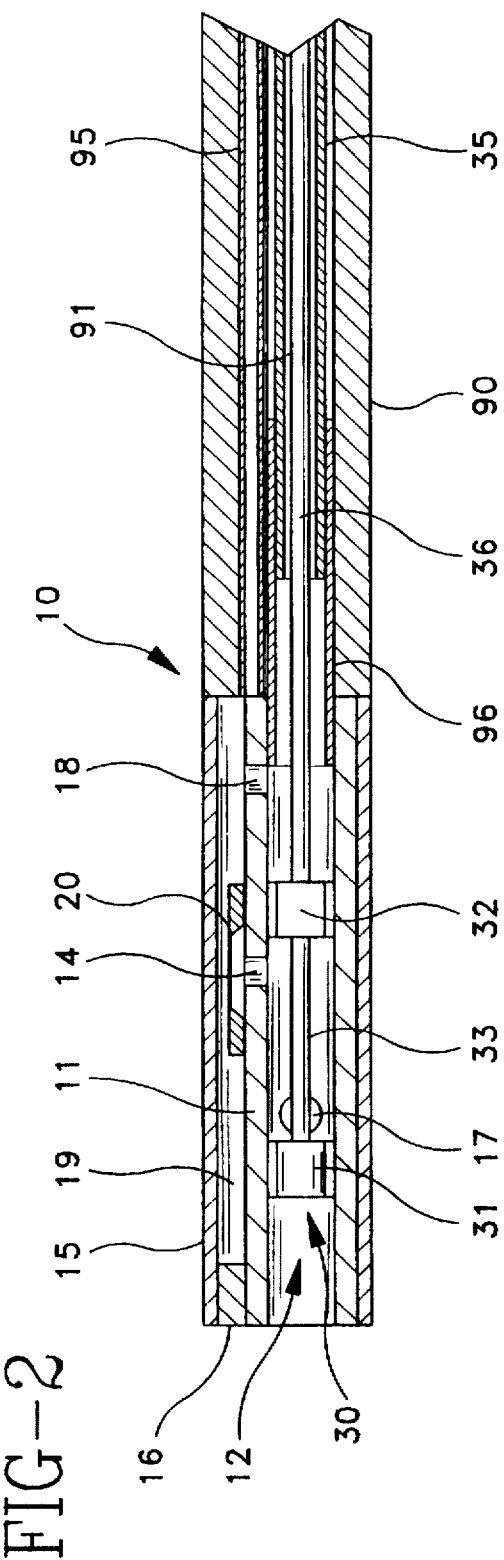
FIG. 2 is a side elevation view in cross-section of a first embodiment of the tip assembly with the rezero apparatus in the measure mode.
Figure 3:
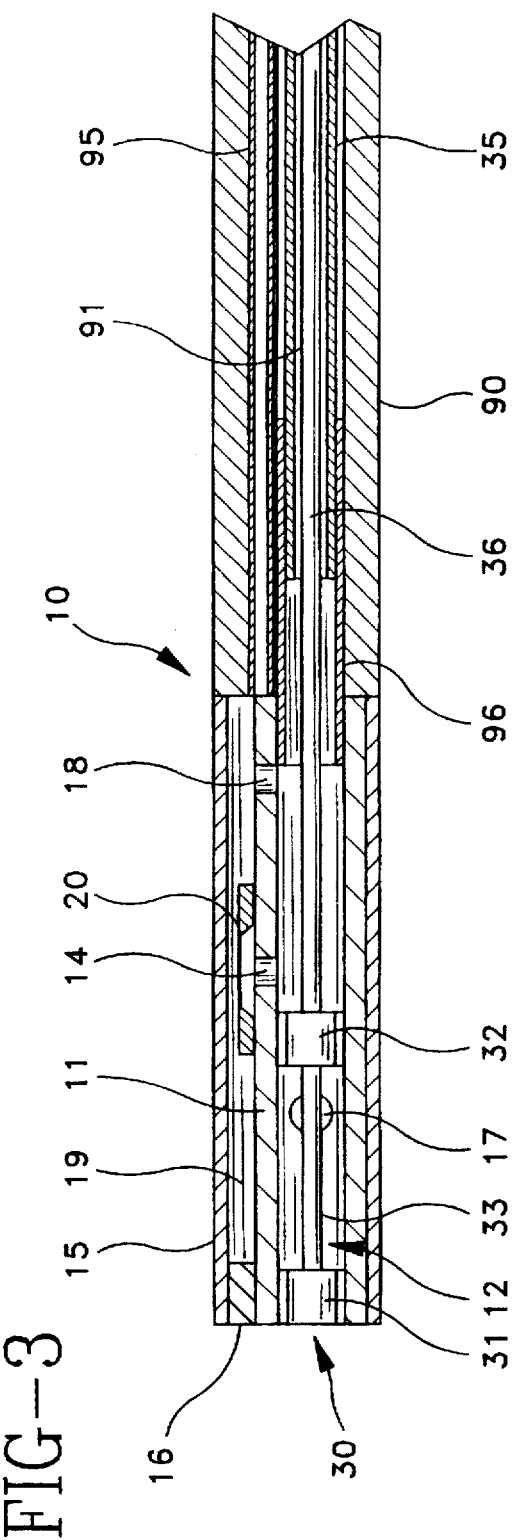
FIG. 3 is a view similar to the view shown in FIG. 2 but with the rezero apparatus in the rezero mode.

In one embodiment of this invention, shown in FIGS. 2 and 3, only one side of pressure transducer 20 is ever exposed to physiologic pressure. This pressure path is explained above. The other side of pressure transducer 20 is always exposed to atmospheric pressure via lumen 19 between sleeve 15 and tube 11. Lumen 19 is vented to atmospheric pressure through a second opening 18 formed in tube 11 into lumen 12. Lumen 12 communicates with lumen 91 of tube 90 through adapter tube 96. Adapter tube 96 is bonded to tube 11 and tube 90 to attach tip assembly 10 to tube 90. The atmospheric pressure path continues proximally through lumen 91 of catheter 90 and out through opening 59 in actuator assembly 50.

A movable seal assembly 30 located in lumen 12 is used to expose one side of pressure transducer 20 to either atmospheric pressure or physiologic pressure. The seal assembly 30 includes two seals 31, 32 formed from a rigid tube made from a non-magnetic alloy or polymer, with a coating of silicone over the outer diameter. The silicone material is applied in an even thickness to form an interference seal with lumen 12 of tube 11. Two seals 31, 32 are attached to actuator rod 33 at a fixed distance by an epoxy or other adhesive.

In the measure mode, see FIG. 2, seal assembly 30 is positioned such that distal seal 31 is distal of opening 17 and proximal seal 32 is between opening 14 and opening 18. Thus, opening 14 and opening 17 are in communication and provide an unobstructed path for the physiologic pressure to reach pressure transducer 20. The pressure path is through opening 17, lumen 12 and opening 14. In the rezero mode, see FIG. 3, seal assembly 30 is moved distally so distal seal 31 is still distal of opening 17 but proximal seal 32 is between opening 17 and opening 14. In this position, both sides of pressure transducer 20 are exposed to atmospheric pressure. One side of pressure transducer 20 is vented to atmospheric pressure via lumen 19, opening 18, lumen 12, and lumen 91 of catheter tube 90 to opening 59 in actuator assembly 50. The other side of pressure transducer 20 is vented to atmospheric pressure via opening 14, lumen 12, and lumen 91 of catheter tube 90 to opening 59 in actuator assembly 50.

In a second embodiment, both sides of pressure transducer 20 can be exposed to physiologic pressure. See FIGS. 5 and 6. In this embodiment, a sidehole 26 is formed in the wall of sleeve 15 over pressure transducer 20 to expose one side of pressure transducer 20 to physiologic pressure. In the measure mode, see FIG. 5, seal assembly 30 is positioned such that distal seal 31 is distal to opening 17 and proximal seal 32 is between opening 17 and opening 14. In this position, the other side of pressure transducer 20 is vented to atmosphere via opening 14, lumen 12 and lumen 91 of catheter tube 90 to opening 59 in actuator assembly 50. The one side of pressure transducer 20 is exposed to physiologic pressure via sidehole 26. In the rezero mode, see FIG. 6, seal assembly 30 is moved proximally so distal seal 31 is still distal of opening 17 but proximal seal 32 is proximal of opening 14. The one side of pressure transducer 20 is still exposed to physiologic pressure via sidehole 26, while the other side of pressure transducer 20 is exposed to physiologic pressure via opening 17, lumen 12 and opening 14. Since pressure transducer 20 is a differential pressure device, this condition is equivalent to exposing both sides of pressure transducer 20 to atmospheric pressure. Although this embodiment is shown in FIGS. 5 and 6 with opening 18, it is to be understood that opening 18 is not necessary to its operation.

Figure 7:
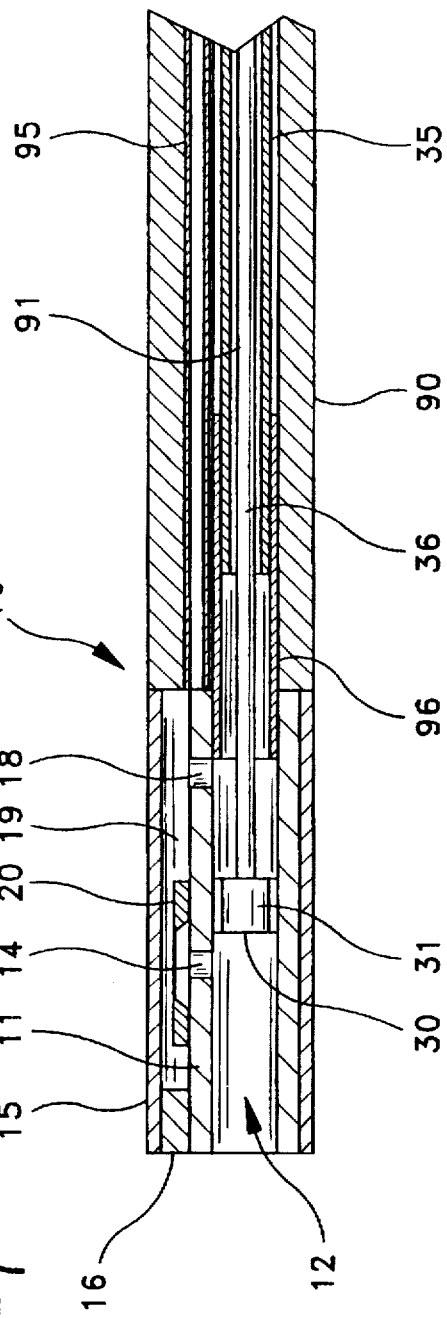
FIG. 7 is a side elevation view in cross-section of a third embodiment of the tip assembly with the rezero apparatus in the measure mode.
Figure 8:
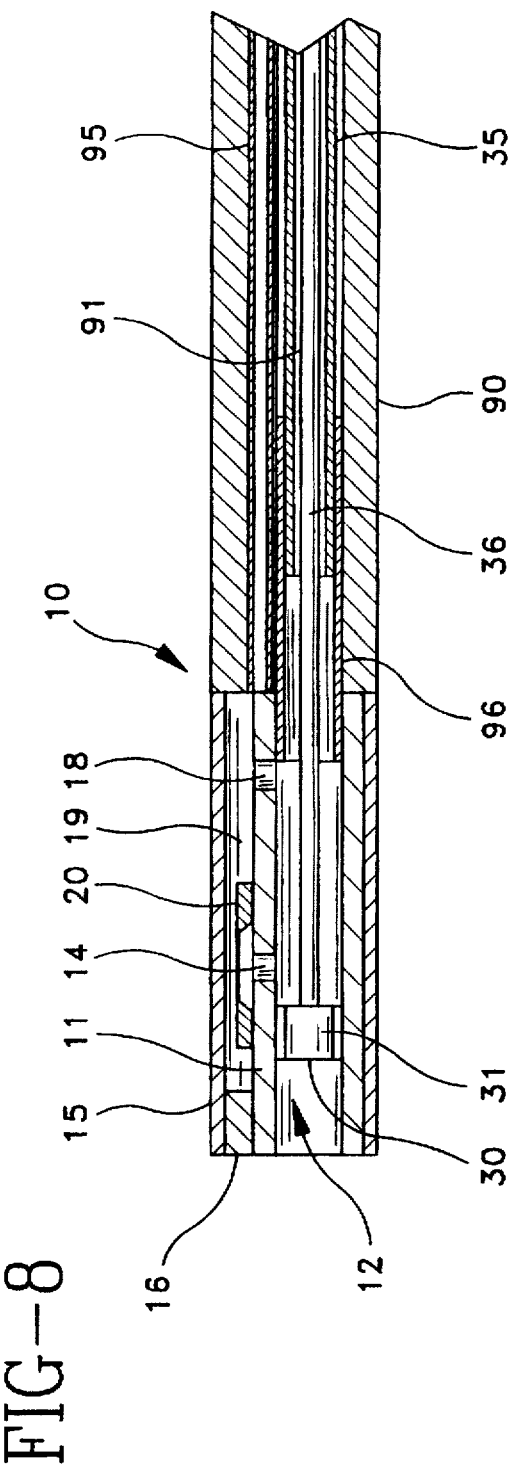
FIG. 8 is a view similar to the view shown in FIG. 7 but with the rezero apparatus in the rezero mode.

In a third embodiment of this invention, seal assembly 30 uses a single seal 31 movable within lumen 12. See FIGS. 7 and 8. In the measure mode, see FIG. 7, seal 31 is proximal to opening 14 and distal to opening 18. In this mode, the one side of pressure transducer 20 is exposed to atmospheric pressure via lumen 19, opening 18, lumen 12 and lumen 91 to opening 59 in actuator assembly 50. The other side of pressure transducer 20 is exposed to physiologic pressure via opening 14 and lumen 12 through the open distal end of tube 11. In the rezero mode, see FIG. 8, seal 31 is distal to opening 14. In this mode, the one side of pressure transducer 20 is exposed to atmospheric pressure as already discussed in connection with the measure mode of this embodiment and the other side of pressure transducer 20 is also exposed to atmospheric pressure via opening 14, lumen 12 and lumen 91 to opening 59 in actuator assembly 50.

The fourth embodiment of this invention is similar to the third embodiment except that sidehole 26 in sleeve 15 exposes pressure transducer 20 to physiologic pressure. See FIGS. 9 and 10. In the measure mode, see FIG. 10, seal 31 is distal of opening 14. In this mode, the one side of pressure transducer 20 is exposed to physiologic pressure via sidehole 26 and the other side of pressure transducer 20 is exposed to atmospheric pressure via opening 14, lumen 12 and lumen 91 to opening 59 in actuator assembly 50. In the rezero mode, see FIG. 9, seal 31 is moved proximal to opening 14. In this mode, the one side of pressure transducer 20 is still exposed to physiologic pressure as discussed above. However, the other side of pressure transducer 20 is also exposed to physiologic pressure via opening 14, lumen 12 and the open distal end of tube 11. Since pressure transducer 20 is a differential pressure device, this condition is equivalent to exposing both sides of pressure transducer 20 to atmospheric pressure.

In all the described embodiments, tip assembly 10 is connected to the distal end of tube 90. Tube 90 is preferably formed from a silicone elastomer and defines a single lumen 91 therethrough. Adapter tube 96 extends proximally of tip assembly 10 and is bonded within lumen 91 of tube 90. Preferably a silicone adhesive is used. Adapter tube 96 is preferably formed from a non-magnetic alloy. Lumen 91 houses actuator rod 36, actuator sleeve 35, carrier tube 95 and provides an atmospheric pressure path from tip assembly 10 to actuator assembly 50. Carrier tube 95 is preferably a polymer extrusion and carries conductor wires (not shown) from pressure transducer 20 to the proximal end of the device for connection to a standard hospital monitor (not shown). Actuator sleeve 35 is preferably a wound non-magnetic alloy and houses actuator rod 36. Actuator rod 36 is preferably formed from a highly elastic non-magnetic alloy and is attached to seal assembly 30 at its distal end. The distal end of actuator sleeve 35 is terminated within adapter tube 96.

Figure 11:
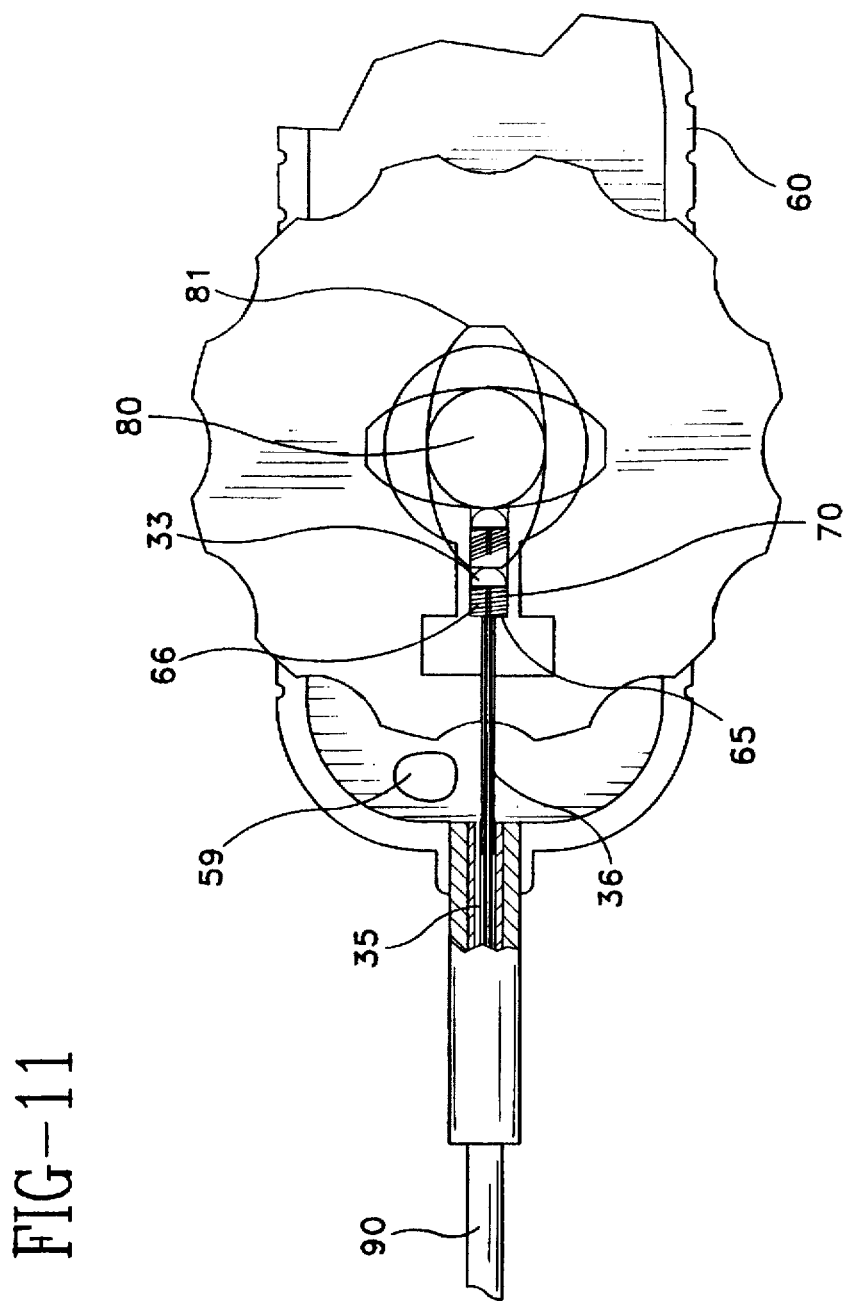
FIG. 11 is a top plan view partially in section of the proximal actuator assembly for the rezero apparatus of this invention.

The proximal end of tube 90 is connected to actuator assembly 50. Preferably a silicone adhesive is used. See FIG. 11. Lumen 91 is vented to atmosphere via opening 59 in actuator assembly 50. Actuator sleeve 35 extends through tube 90 into a cut out portion 65 in the actuator housing 60. Actuator rod 36 extends out of actuator sleeve 35 into cut out portion 65. The proximal end of actuator rod 36 includes an enlarged flange 33. Cut out portion 65 defines a distal shoulder 66 therein. A spring 70 is located around actuator rod 36 between shoulder 66 and flange 33 to bias actuator rod 36 toward the proximal end of the device.

An actuator knob 80 having a cam 81 located about its axis is connected to actuator housing 60. Cam 81 is located in abutting relationship to flange 33 of actuator rod 36. Cam 81 is configured to move flange 33 and thus actuator rod 36 distally against the force of spring 70 when actuator knob 80 is rotated. As cam 81 continues to rotate, spring 70 forces flange 33 and thus actuator rod 36 proximally to follow the contour of cam 81. Thus, by properly configuring cam 81, actuator rod 36 and thus seal assembly 30 can be moved proximally or distally the appropriate distance to place the device either in the pressure measurement mode or the rezero mode.

Thus it is seen that an apparatus for use with an in vivo pressure transducer is provided that will allow the pressure transducer to be rezeroed in vivo.

We claim:

1. An in vivo rezero apparatus for a pressure transducer, comprising:

a sleeve defining a first lumen and a second lumen therein;

a pressure transducer having a first side and a second side disposed in one of the first lumen or the second lumen so that the first side of the pressure transducer is in fluid communication with the first lumen and the second side of the pressure transducer is in fluid communication with the second lumen;

a seal disposed in the first lumen and movable between a first position and a second position where in the first position the first side of the pressure transducer is in fluid communication with the exterior of the sleeve via a first opening defined by the sleeve and the second side of the pressure transducer is in fluid communication with the exterior of the sleeve via a second opening proximal of the first opening and in the second position the first side of the pressure transducer and the second side of the pressure transducer are in fluid communication with the exterior of the sleeve via the second opening proximal of the first opening; and a wall disposed in the sleeve separating the first lumen from the second lumen and wherein the wall defines a third opening and a fourth opening therein to place the first lumen in fluid communication with the second lumen and wherein the pressure transducer is disposed over the third opening.

2. The in vivo rezero apparatus for a pressure transducer of claim 1 wherein the first opening is distal of the third opening, the third opening is distal of the fourth opening and the second opening is proximal of the fourth opening.

3. The in vivo rezero apparatus for a pressure transducer of claim 2 wherein the seal includes a proximal seal and a distal seal such that in the first position the distal seal is distal of the first opening and the proximal seal is between the third opening and the fourth opening and in the second position the distal seal is distal of the first opening and the proximal seal is between the third opening and the first opening.

4. An in vivo rezero apparatus for a pressure transducer, comprising:

a sleeve defining a first lumen and a second lumen therein, a pressure transducer having a first side and a second side disposed in one of the first lumen or the second lumen so that the first side of the pressure transducer is in fluid communication with the first lumen and the second side of the pressure transducer is in fluid communication with the second lumen;

a seal disposed in the first lumen and movable between a first position and a second position where in the first position the first side of the pressure transducer is in fluid communication with the exterior of the sleeve via a first opening defined by the sleeve and the second side of the pressure transducer is in fluid communication with the exterior of the sleeve via a second opening proximal of the first opening and in the second position the first side of the pressure transducer and the second side of the pressure transducer are in fluid communication with the exterior of the sleeve via the second opening proximal of the first opening; and a wall disposed in the sleeve separating the first lumen from the second lumen and wherein the wall defines a third opening therein to place the first lumen in fluid communication with the second lumen and wherein the pressure transducer is disposed over the third opening.

5. The in vivo rezero apparatus for a pressure transducer of claim 4 wherein the third opening is between the first opening and the second opening.

6. The in vivo rezero apparatus for a pressure transducer of claim 5 wherein when the seal is in the first position, the seal is between the third opening and the second opening and when the seal is in the second position, the seal is between the third opening and the first opening.

7. An in vivo rezero apparatus for a pressure transducer, comprising:

a sleeve defining a first lumen and a second lumen therein;

a pressure transducer having a first side and a second side disposed in one of the first lumen or the second lumen so that the first side of the pressure transducer is in fluid communication with the first lumen and the second side of the pressure transducer is in fluid communication with the second lumen;

a seal disposed in the first lumen and movable between a first position and a second position where in the first position the first side of the pressure transducer is in fluid communication with the exterior of the sleeve via a first opening defined by the sleeve and the second side of the pressure transducer is in fluid communication with the exterior of the sleeve via a second opening proximal of the first opening and in the second position the first side of the pressure transducer and the second side of the pressure transducer are in fluid communication with the exterior of the sleeve via the second opening proximal of the first opening, wherein the seal is connected to an actuator rod extending proximal of the seal.

8. The in vivo rezero apparatus for a pressure transducer of claim 7 wherein the actuator rod includes a proximal end disposed in a housing between a spring and a rotatable cam such that the spring biases the proximal end of the actuator rod against the rotatable cam.

9. An in vivo rezero apparatus for a pressure transducer, comprising:

a sleeve defining a first lumen and a second lumen therein and further defining a sidehole therein;

a pressure transducer having a first side and a second side disposed in one of the first lumen or the second lumen adjacent to the sidehole so the first side of the pressure transducer is in fluid communication with the first lumen;

a seal disposed in the first lumen and movable between a first position and a second position where in the first position the second side of the pressure transducer is in fluid communication with the exterior of the sleeve via the sidehole and the first side of the pressure transducer is in fluid communication with the exterior of the sleeve via a first opening proximal of the sidehole and in the second position the first side of the pressure transducer is in fluid communication with the exterior of the sleeve via a second opening defined by the sleeve distal of the first opening and the second side of the pressure transducer is in fluid communication with the exterior of the sleeve via the sidehole; and a wall disposed in the sleeve separating the first lumen from the second lumen and wherein the wall defines a third opening therein to place the first lumen in fluid communication with the second lumen and where the pressure transducer is disposed over the third opening.

10. The in vivo rezero apparatus for a pressure transducer of claim 9 wherein the sidehole is proximal of the second opening and the sidehole is distal of the first opening.

11. The in vivo rezero apparatus for a pressure transducer of claim 10 wherein the seal includes a proximal seal and a distal seal such that in the first position the distal seal is distal of the second opening and the proximal seal is between the second opening and the third opening and in the second position the distal seal is distal of the second opening and the proximal seal is proximal of the third opening.

12. The in vivo rezero apparatus for a pressure transducer of claim 10 wherein when the seal is in the first position the seal is between the third opening and the second opening and when the seal is in the second position the seal is between the first opening and the third opening.

13. An in vivo rezero apparatus for a pressure transducer, comprising:
   a sleeve defining a first lumen and a second lumen therein and further defining a sidehole therein;
   a pressure transducer having a first side and a second side disposed in one of the first lumen or the second lumen adjacent to the sidehole so the first side of the pressure transducer is in fluid communication with the first lumen;
   a seal disposed in the first lumen and movable between a first position and a second position where in the first position the second side of the pressure transducer is in fluid communication with the exterior of the sleeve via the sidehole and the first side of the pressure transducer is in fluid communication with the exterior of the sleeve via a first opening proximal of the sidehole and in the second position the first side of the pressure transducer is in fluid communication with the exterior of the sleeve via a second opening defined by the sleeve distal of the first opening and the second side of the pressure transducer is in fluid communication with the exterior of the sleeve via the sidehole wherein the seal is connected to an actuator rod extending proximal of the seal.

14. The in vivo rezero apparatus for a pressure transducer of claim 13 wherein the actuator rod includes a proximal end disposed in a housing between a spring and a rotatable cam such that the spring biases the proximal end of the actuator rod against the rotatable cam.

15. An in vivo rezero apparatus for a pressure transducer comprising:
   a tube with an exterior wall having a first opening therein and defining a first lumen therein wherein the exterior wall of the tube defines a third opening therein;
   a sleeve having an interior wall affixed over the tube such that at least a portion of the exterior wall and a portion of the interior wall are in abutting relationship thereby creating a second lumen between the sleeve and the tube;
   a pressure transducer affixed to the wall of the tube over the first opening in the tube;
   a second opening through the portion of the exterior wall of the tube and the portion of the interior wall of the sleeve that are in abutting relationship distal to the first opening; and
   a movable seal within the first lumen and movable between a first position and a second position.

16. The in vivo rezero apparatus of claim 15 wherein when the seal is in the first position the first opening and the second opening are in fluid communication and when the seal is in the second position the first opening and the third opening are in fluid communication.

17. The in vivo rezero apparatus of claim 16 further comprising a means for communicating atmospheric pressure to the first lumen of the tube.

18. The in vivo rezero apparatus of claim 16 further comprising a means for moving the seal between the first position and the second position.

19. An in vivo rezero apparatus for a pressure transducer, comprising:
   a tube with an exterior wall having a first opening therein and defining a first lumen therein;
   a sleeve having an interior wall affixed over the tube such that at least a portion of the exterior wall and a portion of the interior wall are in abutting relationship thereby creating a second lumen between the sleeve and the tube wherein the sleeve defines a sidehole adjacent to the pressure transducer such that one side of the pressure transducer is in fluid communication with the exterior of the sleeve via the sidehole;
   a pressure transducer affixed to the wall of the tube over the first opening in the tube;
   a second opening through the portion of the exterior wall of the tube and the portion of the interior wall of the sleeve that are in abutting relationship distal to the first opening; and
   a movable seal within the first lumen and movable between a first position and a second position.

20. The in vivo rezero apparatus of claim 19 wherein when the seal is in the first position the first opening is in fluid communication with the first lumen and when the seal is in the second position the first opening and the second opening are in fluid communication.

21. The in vivo rezero apparatus of claim 20 further comprising a means for communicating atmospheric pressure to the first lumen of the tube.

22. The in vivo rezero apparatus of claim 20 further comprising a means for moving the seal between the first position and the second position.

23. An in vivo rezero apparatus for a pressure transducer, comprising:
   a tube with a distal portion wherein the tube has an exterior wall with a first opening in the distal portion of the tube and defining a first lumen with an open distal end therein;
   a sleeve having an interior wall affixed over the tube such that at least a portion of the exterior wall and a portion of the interior wall are in abutting relationship thereby creating a second lumen between the sleeve and tube;
   a pressure transducer affixed to the exterior wall of the tube along the distal portion of the tube over the first opening in the tube; and
   a seal disposed within the first lumen in the distal portion of the tube for movement distally and proximally between a first position and a second position.

24. The in vivo rezero apparatus of claim 23 wherein the exterior wall of the tube defines a second opening therein such that when the seal is in the first position the first opening and the open distal end of the tube are in fluid communication and when the seal is in the second position the first opening and the second opening are in fluid communication.

25. The in vivo rezero apparatus of claim 24 further comprising a means for communicating atmospheric pressure to the first lumen of the tube.

26. The in vivo rezero apparatus of claim 24 further comprising a means for moving the seal between the first position and the second position.

27. The in vivo rezero apparatus of claim 23 wherein the sleeve defines a sidehole adjacent to the pressure transducer such that one side of the pressure transducer is in fluid communication with the exterior of the sleeve via the sidehole.

28. The in vivo rezero apparatus of claim 27 wherein when the seal is in the first position the first opening is in fluid communication with the first lumen and when the seal is in the second position the first opening and the open distal end of the tube are in fluid communication.

29. The in vivo rezero apparatus of claim 28 further comprising a means for communicating atmospheric pressure to the first lumen of the tube.

30. The in vivo rezero apparatus of claim 28 further comprising a means for moving the seal between the first position and the second position.

31. An in vivo rezero apparatus for a pressure transducer, comprising:
- a tip assembly having a distal end and a proximal end and including a sleeve having an interior wall and a first tube having an exterior wall and defining a first lumen therein and disposed in the sleeve and affixed thereto in an area where at least a portion of the exterior wall and the interior wall are in abutting relationship to define a second lumen between the first tube and the sleeve;
- a second tube having a proximal end and a distal end affixed to the proximal end of the tip assembly, the second tube defining a third lumen in fluid communication with the first lumen;
- a handle affixed to the proximal end of the second tube; and
- a seal assembly including a distal seal connected to an actuator rod movably disposed in the first lumen and the third lumen.

32. The in vivo rezero apparatus for a pressure transducer of claim 31 wherein the exterior wall defines a first opening and a second opening therein to place the first lumen and the second lumen in fluid communication and a third opening defined by the area where at least a portion of the exterior wall and the interior wall are in abutting relationship and further comprising a pressure transducer disposed in the second lumen over the first opening.

33. The in vivo rezero apparatus for a pressure transducer of claim 32 wherein the seal assembly further includes a proximal seal and a distal seal.

34. The in vivo rezero apparatus for a pressure transducer of claim 31 wherein the exterior wall defines a first opening therein to place the first lumen and the second lumen in fluid communication and wherein the sleeve defines a sidehole therein and further comprising a pressure transducer disposed in the second lumen over the first opening adjacent the sidehole.

35. The in vivo rezero apparatus for a pressure transducer of claim 34 wherein the seal assembly further includes a proximal seal and a distal seal.

36. The in vivo rezero apparatus for a pressure transducer of claim 31 wherein the exterior wall defines a first opening and a second opening therein to place the first lumen in fluid communication with the second lumen and further comprising a pressure transducer disposed in the second lumen over the first opening.

37. The in vivo rezero apparatus for a pressure transducer of claim 31 wherein the exterior wall defines an opening therein to place the first lumen in fluid communication with the second lumen and wherein the sleeve defines a sidehole therein and further comprising a pressure transducer disposed in the second lumen over the first opening adjacent to the sidehole.

* * * * *